United States Patent [19]

Lattanzi et al.

[11] Patent Number: 5,441,933
[45] Date of Patent: Aug. 15, 1995

[54] PHARMACEUTICAL COMPOSITIONS AND DOSAGE FORMS FOR THE ORAL ADMINISTRATION OF CALCITONIN

[75] Inventors: Filippo Lattanzi, Siena; Maurizio Cecchettin, Brescia; Riccardo Vanni, Siena, all of Italy

[73] Assignee: Sciavo S.P.A., Siena, Italy

[21] Appl. No.: 640,811

[22] Filed: Jan. 14, 1991

[30] Foreign Application Priority Data

Jan. 19, 1990 [IT] Italy .................... 19112/90

[51] Int. Cl.$^6$ ................... A61K 38/23; C07K 14/585
[52] U.S. Cl. ................................ 514/12; 514/2; 530/300; 530/307
[58] Field of Search .................... 514/2, 12; 530/300, 530/307

[56] References Cited

U.S. PATENT DOCUMENTS

| | | | |
|---|---|---|---|
| 4,151,276 | 4/1979 | Caulin et al. | 530/307 |
| 4,530,838 | 7/1985 | Evans et al. | 514/11 |
| 4,663,309 | 5/1987 | Kaiser et al. | 530/307 |
| 5,183,802 | 2/1993 | Aliverti et al. | 514/2 |
| 5,288,497 | 2/1994 | Stanley et al. | 424/440 |

FOREIGN PATENT DOCUMENTS 61-126034 6/1986 Japan .
62-10020 1/1987 Japan .

OTHER PUBLICATIONS

Nakada et al., "The Effect of Additives on the Oral Mucosal Absorption of Human Calcitonin in Rats", *J. Pharmacobio-Dyn.* 11: 395–401, 1988.

*Primary Examiner*—Stephen G. Walsh
*Attorney, Agent, or Firm*—Birch, Stewart, Kolasch & Birch

[57] ABSTRACT

New pharmaceutical compositions containing a calcitonin as active principle and suitable fop opal administration in the form of perbuccal and sublingual tablets ape described, in which the active principle is homogenized with a mixture of solid excipients, said excipients consisting of a diluent, a lubricant, a disintegrating agent in the case of sublingual tablets, and a binder in the case of perbuccal tablets. Said compositions enable the same pattern of hematic levels to be obtained fop the same unit dose as obtainable by conventional intramuscular administration.

1 Claim, 3 Drawing Sheets

PHARMACEUTICAL COMPOSITIONS AND DOSAGE FORMS FOR THE ORAL ADMINISTRATION OF CALCITONIN

This invention relates to pharmaceutical compositions containing a calcitonin as active principle, homogenized with a mixture of solid excipients suitable for oral administration in the form of tablets.

In particular, the present invention relates to sublingual and perbuccal tablets suitable for the oral administration of a calcitonin, obtained using said pharmaceutical compositions.

The calcitonins constitute a known class of pharmacologically active long-chain polypeptides the use of which has been well described in the literature. Various calcitonins, including for example salmon and eel calcitonin, are currently used for treating for example Paget's disease, Sudek's disease and osteoporosis.

However, the preparation of an appropriate and effective means of calcitonin administration has caused numerous difficulties. In this respect, as in the case of polypeptides in general, when administered orally they are easily degraded by the proteolytic enzymes present in the gastrointestinal tract, which rapidly hydrolyze them to oligopeptides free of pharmacological activity, whereafter they are metabolized by the liver.

For these reasons, the pharmaceutical forms in which calcitonins are commonly sold are suitable only for intramuscular or intravenous administration of the active principle.

Such a method of administration is however inconvenient, especially in the case of lengthy treatment.

In this respect it has been found that after prolonged parenteral calcitonin treatment, side effects such as diarrhea, sudden perspiring, hot flushes and a sense of vexation arise.

Other methods of calcitonin administration have been proposed in the art, such as nasal and rectal. These administration methods involve however considerable problems.

For example, nasal clinical treatment using a nasal spray results in very low absorption of the active principle, even if high doses are used. Specifically, using doses four times greater than those used for parenteral administration, an absorption of 30% is obtained.

In addition, it has been observed that the absorption is further reduced in elderly people, who represent those most afflicted by the aforesaid pathologies.

The possibility of administering these active principles orally has been the object of considerable study in recent years. However, the results obtained have shown that even in the case of adequately protected calcitonins a rapid degradation of the active principle occurs, with a corresponding low level of absorption.

The object of the present invention is consequently to find other calcitonin administration means which overcome the drawbacks of the known art.

It has now been found that an effective clinical treatment can be achieved by administering calcitonins orally in the form of perbuccal and sublingual tablets.

More specifically, the applicant has found, in accordance with the teachings of the present invention, that hematic calcitonin levels equivalent to those obtained by intramuscular administration in the usual doses can be obtained by oral administration of a calcitonin in the form of perbuccal or sublingual tablets in doses which fall within the limits of tolerability and practicality.

Oral perbuccal or sublingual administration is a simple and painless method which can be easily used by the patient himself, employing perbuccal or sublingual tablets.

Although such administration is preferable to parenteral administration, such as by injection as commonly practised up to the present time, the preparation of a composition appropriate to this type of administration presents certain difficulties.

One of these, which is particularly delicate in relation to oral administration of complex active principles such as the calcitonins, is to provide a totally compatible and effective means.

In this respect, a pharmaceutical composition for oral application in the form of sublingual and perbuccal tablets must be well tolerated, particularly at the site of its application, must not irritate the mucosa, and must not result in a too rapid disintegration of the tablet in the case of perbuccal tablets, which disintegration furthermore must be incomplete or absent in the case of sublingual tablets.

In addition the results obtained must be uniform, with corresponding uniformity of bioavailability of the active principle.

The concept of bioavailability of a pharmaceutical product has become of great interest in recent years as it is directly related to therapeutic efficiency. Bioavailability can be defined as the quantity of medicament absorbed into the blood from an administered pharmaceutical product. The bioavailability of a pharmacologically active compound depends on numerous factors, such as the excipients used for preparing the pharmaceutical compositions, the technology used for preparing the dosage forms and the physico-chemical properties of the active principle. Thus two products of the same type (tablets) containing the same quantity of the same active ingredient can show different degrees of bioavailability, i.e. they are chemically equivalent but not necessarily bioequivalent. For two chemically identical products to be bioequivalent they must attain the same plasmatic concentration within the same time.

The present invention therefore provides pharmaceutical compositions containing a calcitonin as active principle and suitable for oral administration in the form of perbuccal and sublingual tablets in which said calcitonin is homogenized with a mixture of solid excipients, said excipients consisting of a diluent, a lubricant, a disintegrating agent in the case of sublingual tablets, and a binder in the case of perbuccal tablets.

The invention also provides unit dosage forms for the oral administration of a calcitonin in the form of perbuccal and sublingual tablets, prepared using said compositions.

Further aspects of the present invention will be apparent from the following description and examples.

Specifically, the pharmaceutical compositions of the present invention consist of a homogenate of the active principle, possibly mixed with a suitable stabilizer, with a mixture of solid ingredients, said mixture consisting of:

1) a completely soluble diluent consisting of mannitol and one or more sugars;

2) a disintegrating agent in the case of sublingual tablets, or a binder to slow down dissolution in the case of perbuccal tablets; and 3) a lubricant.

The active principle for use in the formulations of the present invention can be chosen from calcitonins of natural or synthetic origin such as salmon calcitonin (SCT), eel calcitonin (ECT) or pig calcitonin, or synthetic analogues such as (Asu$^{1,7}$)ECT commonly known as carbocalcitonin.

The quantity of active ingredient to be used in the composition depends on the type of calcitonin used, the disease to be treated, the desired frequency of administration and the desired effect. Generally, active principle quantities of between 20 and 800 I.U. and preferably between 50 and 500 I.U. per tablet (100–150 g) are used.

Diluents suitable for the purposes of the present invention can be chosen from mannitol, lactose, saccharose and a mixture of lactose and saccharose in a quantity of between 20 and 70% and preferably between 30 and 55% by weight with respect to the total weight of the tablet.

Disintegrating agents suitable for the purposes of the present invention are chosen from starch, sodiumcarboxymethyl starch, carboxymethylcellulose, microcrystalline cellulose, crospovidone, amberlite and alginic acid in a quantity of between 1 and 15%, and preferably 5–10% in the case of microcrystalline cellulose and 1–3% in the case of the other disintegrating agents, by weight with respect to the total weight of the tablet.

Binders able to delay solubilization of the perbuccal tablet are chosen generally from gum arabic and cellulose derivatives such as hydroxypropylcellulose and hydroxypropylmethylcellulose in a quantity of between 1 and 25% and preferably between 5 and 10% by weight with respect to the total weight of the tablet.

Lubricants are chosen from magnesium stearate, aluminum stearate, stearic acid, high molecular weight PEG and talc, in a concentration of between 0.3 and 5% and preferably between 0.5 and 2%.

According to the present invention the pharmaceutical compositions for the preparation of sublingual and perbuccal tablets can also contain coloring and flavoring agents.

The compositions according to the present invention are well tolerated and do not induce undesirable side effects.

BRIEF DESCRIPTION OF THE DRAWINGS

The results obtained are shown in FIGS. 1–3.

In addition the results obtained indicate the appearance of calcitonin in the blood within 4–5 minutes of administration. In particular, the compositions described in Examples 1 and 2 for the preparation of sublingual tablets are distinguished by a bioavailability with in the first case peaks of lesser but constant intensity (150–160 pg/ml), and in the second case a peak of greater intensity (200–210 pg/ml) and a more rapid decline, but which remains at a good level.

One characteristic of the compositions of the present invention and in particular of this method of administration is the surprising uniformity of the results and hence of the bioavailability of the active principle.

The absorption of the active principle, which is practically immediate and less sensitive to variables, is between 70% and 90%.

These dosage forms offer advantages such as stability, accuracy and precision together with good bioavailability of the active principle.

When the best formulation has been established, the tablets can be prepared by directly compressing the pulverized or granulated mixture of the active principle and excipients using currently available equipment for this purpose.

The following examples illustrate in greater detail some formulations and some unit dosage forms representative of the present invention, and the experimental results obtained on administering some of these.

EXAMPLE 1

Sublingual Tablets

Sublingual tablets weighing approximately 100 mg were prepared having the following composition:

| | |
|---|---|
| ECT | 50.00 IU |
| Lactose | 42.00 mg |
| Saccharose | 40.00 mg |
| Microcrystalline cellulose | 6.00 mg |
| Amberlite IRP88 | 2.00 mg |
| Magnesium stearate | 0.90 mg |

These tablets were administered to a group of 18 healthy volunteers. When placed under the tongue the tablets, which were odorless and of pleasant taste, dissolved within one minute at the most.

Blood samples were taken at time 0 and at 5, 10, 60, 90 and 120 minutes after administration.

The calcitonin concentration in the serum was determined by radio-immunological assay.

Figure 1:
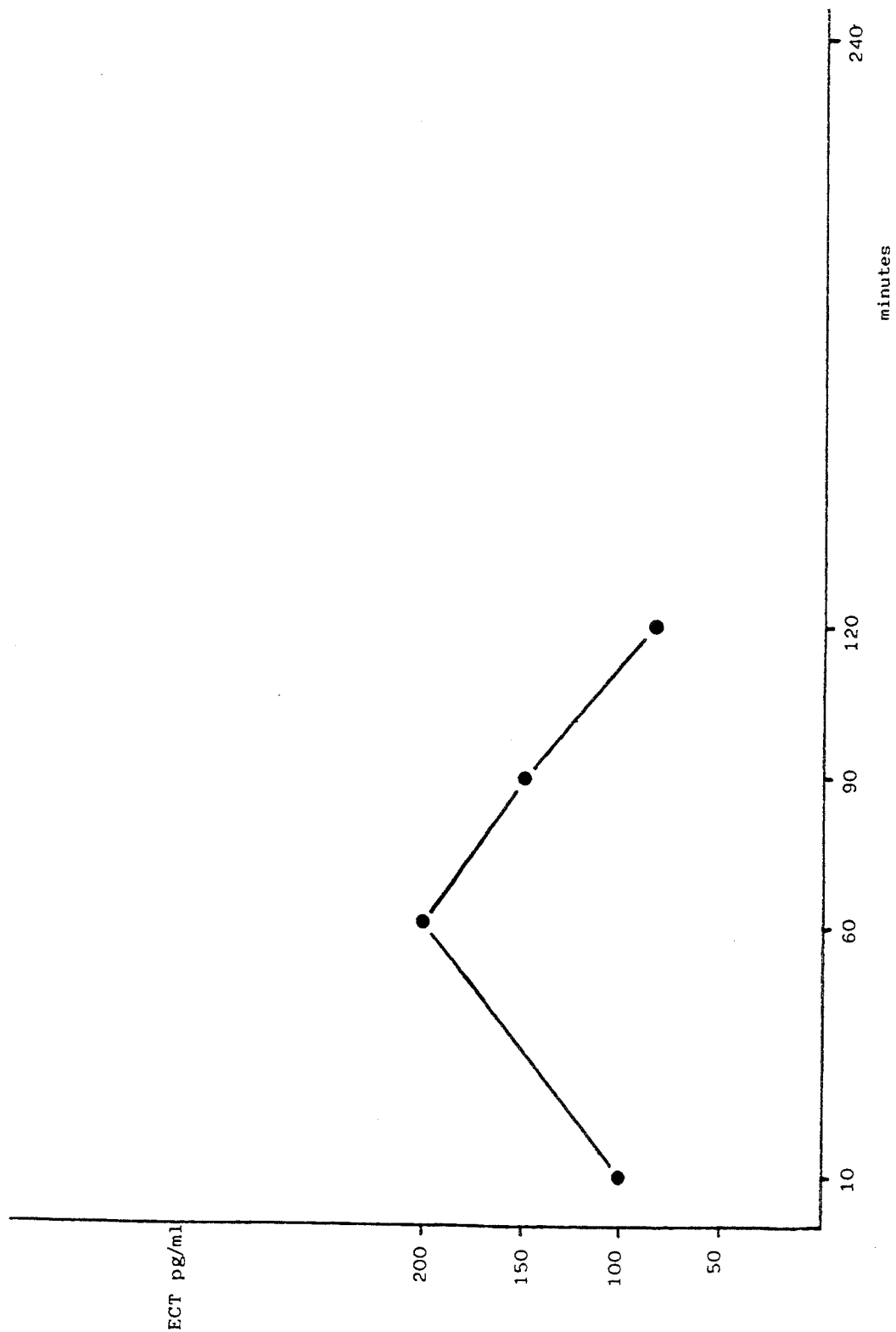
FIG. 1 shows results from Example 1.

The mean results for the 18 volunteers are shown in FIG. 1.

These results show the appearance of eel calcitonin in the blood within 4–5 minutes from administration.

Side effects did not appear.

EXAMPLE 2

Sublingual tablets weighing approximately 100 mg were prepared having the following composition:

| | |
|---|---|
| ECT | 50.00 IU |
| Ludipress | 50.00 mg |
| Saccharose | 40.00 mg |
| Microcrystalline cellulose | 9.00 mg |
| Magnesium stearate | 1.00 mg | where ludipress is lactose plus polyvinylpyrrolidne (PVP).

These tablets were administered to a group of 18 volunteers, of whom 6 were healthy and 12 were osteoporotic. When placed under the tongue the tablets, which were odorless and of pleasant taste, dissolved within one minute at the most.

Blood samples were taken at time 0 and at 5, 10, 20, 30, 60, 90 and 120 minutes after administration.

The calcitonin concentration in the serum was determined by radio-immunological assay.

Figure 2:
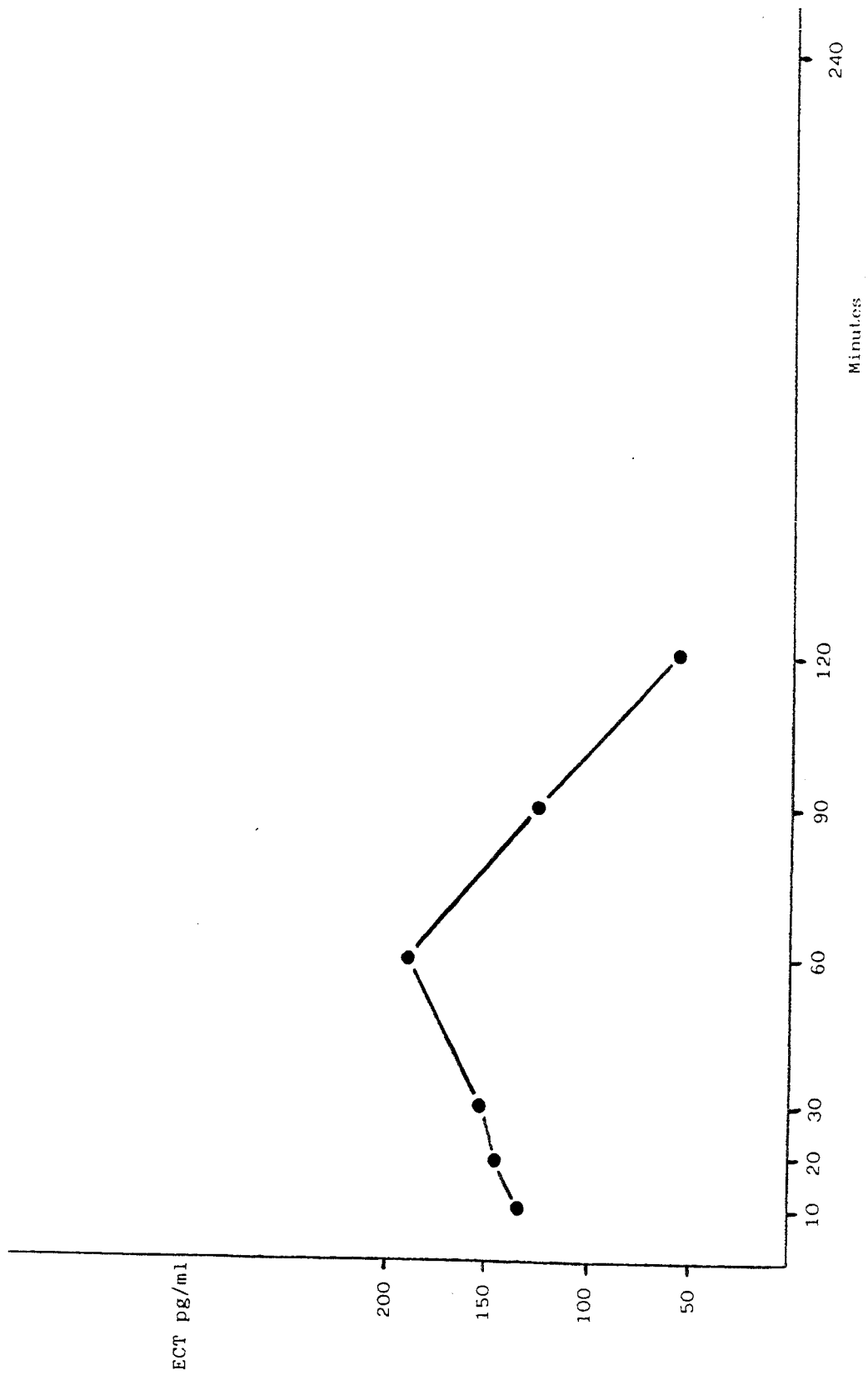
FIG. 2 shows results from Example 2

The mean results for the 18 volunteers are shown in FIG. 2.

These results show the appearance of salmon calcitonin in the blood within 4–5 minutes from administration. Side effects did not appear.

EXAMPLES 3–14

These examples describe formulations containing a calcitonin as active principle and usable fop opal administration in the form of sublingual tablets.

The quantities indicated represent a formulation usable for preparing 1000 tablets each weighing about 100 mg.

| 3) ECT | 50,000 I.U. |
|---|---|
| Lactose | 47.00 g |
| Saccharose | 40.00 g |
| Microcrystalline cellulose | 10.00 g |
| Amberlite IRP-88 | 0.50 g |
| Sodium carboxymethyl starch | 1.50 g |
| Magnesium stearate | 1.00 g |
| 4) ECT | 50,000 I.U. |
| Lactose | 47.00 g |
| Saccharose | 40.00 g |
| Microcrystalline cellulose | 10.00 g |
| Amberlite IRP-88 | 2.00 g |
| Magnesium stearate | 1.00 g |
| 5) ECT | 50,000 I.U. |
| Lactose | 50.00 g |
| Saccharose | 32.00 g |
| Microcrystalline cellulose | 6.00 g |
| Explotab | 2.00 g |
| Magnesium stearate | 0.90 g |
| where Explotab is sodiumcarboxymethyl starch | |
| 6) SCT | 50,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |
| 7) ECT | 50,000 I.U. |
| Lactose | 42.00 g |
| Saccharose | 40.00 g |
| Microcrystalline cellulose | 6.00 g |
| Amberlite IRP-88 | 2.00 g |
| 8) SCT | 50,000 I.U. |
| Ludipress | 50.00 g |
| Saccharose | 40.00 g |
| Microcrystalline cellulose | 9.00 g |
| Magnesium stearate | 1.00 g |
| 9) (Asu$^{1,7}$) ECT | 50,000 I.U. |
| Ludipress | 50.00 g |
| Saccharose | 40.00 g |
| Microcrystalline cellulose | 9.00 g |
| Magnesium stearate | 1.00 g |
| 10) ECT | 100,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |
| 11) ECT | 150,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |
| 12) SCT | 100,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |
| 13) SCT | 150,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |
| 14) (Asu$^{1,7}$) ECT | 100,000 I.U. |
| Lactose | 42.00 g |
| Saccharose | 40.00 g |
| Microcrystalline cellulose | 6.00 g |
| Amberlite IRP-88 | 2.00 g |
| Magnesium stearate | 0.90 g |

EXAMPLE 15

Perbuccal Tablets

Perbuccal tablets weighing about 150 mg were prepared having the following composition:

| ECT | 50.00 I.U. |
|---|---|
| Lactose | 69.75 mg |
| Saccharose | 69.75 mg |
| Hydroxypropylmethylcellulose K100M | 7.50 mg |
| Mg stearate | 1.50 mg |
| Talc | 1.50 mg |

These tablets were administered to a group of 10 volunteers, of whom 4 were healthy and 6 were osteoporotic. When placed between the upper gingiva and the cheek the tablets, which were odorless and of pleasant taste, dissolved within a time variable between 30 and 60 minutes without leaving residues and without impeding phonation.

Blood samples were taken at time 0 and at 15, 30, 60 and 120 minutes after administration.

The calcitonin concentration in the serum was determined by radio-immunological assay.

Figure 3:
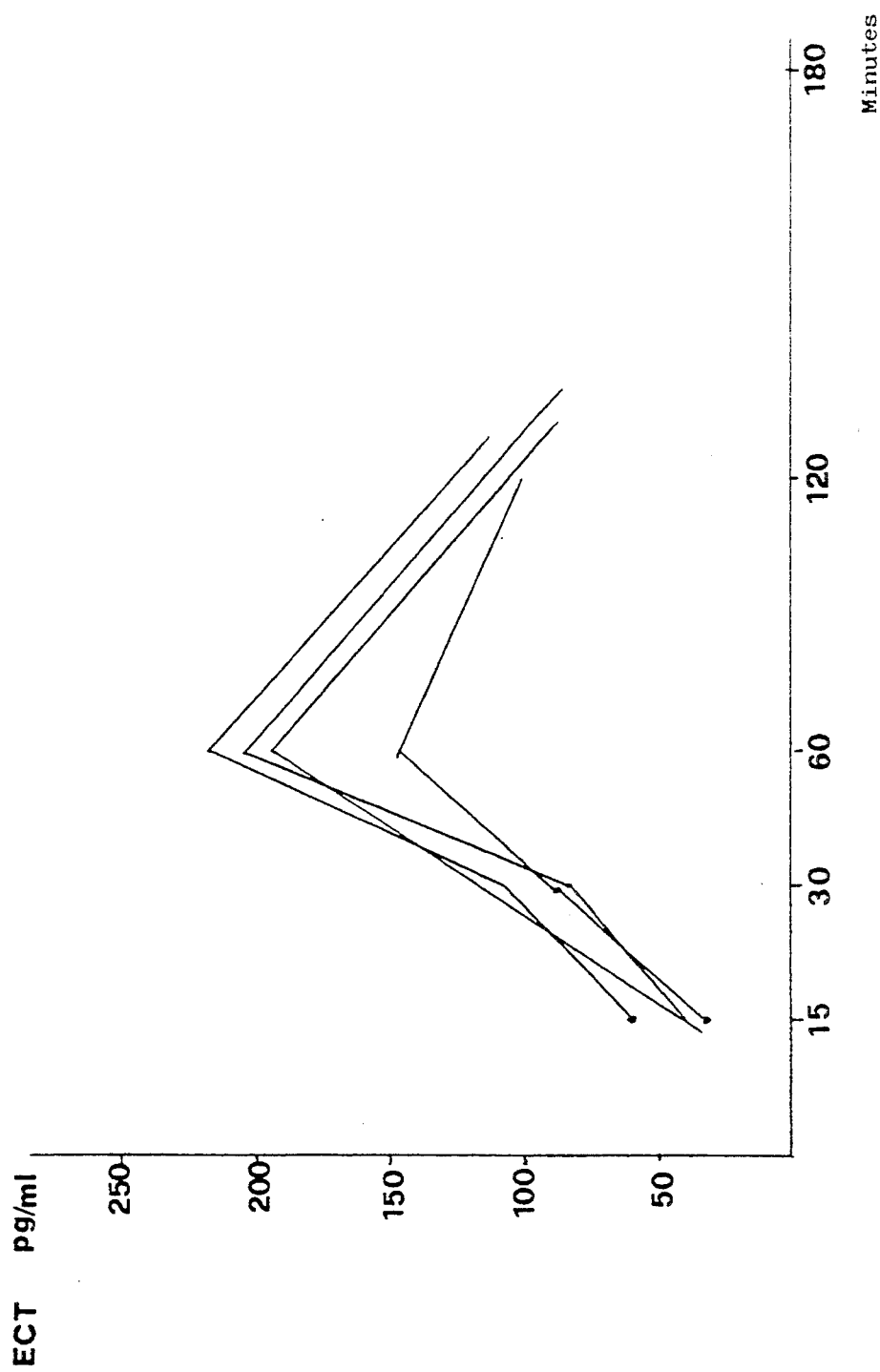
FIG. 3 shows results obtained with perbuccal tablets.

The mean results for the 10 volunteers are shown in FIG. 3. (The figure shows only four lines because some results were overlapping.)

These results show the appearance of eel calcitonin in the blood within 10 minutes from administration. The ECT concentration remained within acceptable values for 180 minutes.

Side effects did not appear.

EXAMPLES 16-28

These examples describe formulations containing a calcitonin as active principle and usable for oral administration in the form of perbuccal tablets.

The quantities indicated represent a formulation usable for preparing 1000 tablets each weighing about 150 mg.

| 16) ECT | 50,000 I.U. |
|---|---|
| Lactose | 66.00 g |
| Saccharose | 66.00 g |
| Hydroxypropylmethylcellulose | 15.00 g |
| Mg stearate | 1.50 g |
| Talc | 1.50 g |
| 17) ECT | 50,000 I.U. |
| Lactose | 66.00 g |
| Saccharose | 66.00 g |
| Hydroxypropylmethylcellulose K100M | 15.00 g |
| Mg stearate | 1.50 g |
| Talc | 1.50 g |
| 18) ECT | 50,000 I.U. |
| Lactose | 68.50 g |
| Saccharose | 68.50 g |
| Gum arabic | 10.00 g |
| Mg stearate | 1.50 g |
| Talc | 1.50 g |
| 19) ECT | 50,000 I.U. |
| Lactose | 69.75 g |
| Saccharose | 69.75 g |
| Hydroxypropylmethylcellulose K100M | 3.75 g |
| Hydroxypropylmethylcellulose K4Ms | 3.75 g |
| Mg stearate | 1.50 g |
| Talc | 1.50 g |
| 20) ECT | 50,000 I.U. |
| Lactose | 69.75 g |
| Saccharose | 69.75 g |
| Hydroxypropylmethylcellulose K100M | 5.00 g |
| Hydroxypropylmethylcellulose K4Ms | 2.50 g |
| Mg stearate | 1.50 g |
| Talc | 1.50 g |
| 21) ECT | 100,000 I.U. |
| Lactose | 69.75 g |
| Saccharose | 69.75 g |
| Hydroxypropylmethylcellulose K100M | 7.50 g |
| Mg stearate | 1.50 g |
| Talc | 1.50 g |

| | | |
|---|---|---|
| 22) ECT | 150,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 23) SCT | 50,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 24) (Asu$^{1,7}$) ECT | 50,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 25) SCT | 100,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 26) (Asu$^{1,7}$) ECT | 100,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 27) SCT | 150,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |
| 28) (Asu$^{1,7}$) ECT | 150,000 | I.U. |
| Lactose | 69.75 | g |
| Saccharose | 69.75 | g |
| Hydroxypropylmethylcellulose K100M | 7.50 | g |
| Mg stearate | 1.50 | g |
| Talc | 1.50 | g |

We claim:

1. A method of administering calcitonin which comprises giving, by perbuccal or sublingual route, a patient in need of calcitonin, a calcitonin composition which consists of
   a) calcitonin, a diluent selected from the group consisting of mannitol, lactose, saccharose and a mixture of lactose and saccharose in a quantity of between 20 and 70% with respect to the total weight of the composition, a lubricant selected from the group consisting of magnesium stearate, aluminum stearate, stearic acid, high molecular weight PEG and talc, and a binder selected from the group consisting of gum arabic and cellulose derivatives for the administration by perbuccal route, or
   b) calcitonin, a diluent selected from the group consisting of mannitol, lactose, saccharose and a mixture of lactose and saccharose in a quantity of between 20 and 70% with respect to the total weight of the composition, a lubricant selected from the group consisting of magnesium stearate, aluminum stearate, stearic acid, high molecular weight PEG and talc, and a disintegrant selected from the group consisting of starch, sodium carboxymethyl starch, carboxymethylcellulose, microcrystalline cellulose, crospovidone, amberlite and alginic acid for the administration by sublingual route.

* * * * *